United States Patent [19]

Van Rheenen et al.

[11] 4,154,748

[45] May 15, 1979

[54] PHOSPHATE CATALYZED ACYLATION OF STEROIDAL TERTIARY ALCOHOLS

[75] Inventors: Verlan H. Van Rheenen; James B. Heather, both of Portage, Mich.

[73] Assignee: The Upjohn Company, Kalamazoo, Mich.

[21] Appl. No.: 870,889

[22] Filed: Jan. 20, 1978

[51] Int. Cl.$^2$ ............ C07J 5/00; C07J 1/00; C07J 7/00

[52] U.S. Cl. ............ 260/397.4; 260/397.45; 260/397.47

[58] Field of Search ............ 260/397.45, 397.4, 397.47

[56] References Cited

U.S. PATENT DOCUMENTS

| | | | |
|---|---|---|---|
| 2,695,907 | 11/1954 | Murray et al. | 260/397.45 |
| 2,753,360 | 7/1956 | Kaspar et al. | 260/397.4 |
| 2,781,369 | 2/1957 | Oliveto et al. | 260/397.45 |
| 2,959,603 | 11/1960 | Gould et al. | 260/397.45 |
| 3,004,991 | 10/1961 | Petrow | 260/397.4 |
| 3,026,335 | 3/1962 | Fried | 260/397.4 |
| 3,061,616 | 10/1962 | Camerino et al. | 260/397.4 |
| 3,297,729 | 1/1967 | Mancini et al. | 260/397.4 |
| 3,409,643 | 11/1968 | Shapiro | 260/397.5 |
| 3,422,193 | 1/1969 | Shapiro et al. | 260/397.45 X |
| 3,678,082 | 7/1972 | Dryden, Jr. | 260/397.5 |
| 3,721,687 | 3/1973 | Elks et al. | 260/397.45 |

OTHER PUBLICATIONS

Chem. Abstracts 51:P8138a.
Chem. Abstracts 55:P.7362g.
Carbohyd. Res. 6, 237, (1968).
Fatiadi, A., Carbohyd. Res. 1968, 6 (2), 237–240.
Djerassi et al., J. Am. Chem. Soc., 77, 3826 (1955).
R. Vitlotti et al., J. Am. Chem. Soc., 81, 4566 (1959).
Kondo et al., Journ. Amer. Chem. Soc., 86, 736–737.
Dodson et al., Journ. Amer. Chem. Soc., 80, p. 6148.

*Primary Examiner*—Ethel G. Love
*Attorney, Agent, or Firm*—Bruce Stein

[57] ABSTRACT

The process of the invention permits acylation of hindered steroidal tertiary alcohols without the undesirable side reactions which accompany previously known acylation reactions.

75 Claims, No Drawings

PHOSPHATE CATALYZED ACYLATION OF STEROIDAL TERTIARY ALCOHOLS

BACKGROUND OF THE INVENTION

Acylation of hindered tertiary alcohols proceeds with difficulty because of both the reduced reactivity of the tertiary alcohol to acylation and the hindered nature of the hydroxyl group.

In 17α-hydroxy steroids such as the corticoids and 17α-hydroxyprogesterones, the 17α-hydroxy group is a tertiary alcohol and is very hindered. Acylation of the 17α-hydroxy group of the corticoids and 17α-hydroxyprogesterones requires vigorous conditions and is generally accompanied by various undesirable side reactions.

D-homo rearrangement occurs under both basic (e.g., acetic anhydride-pyridine) or acidic (e.g., acetic anhydride-p-TSA) acylation conditions. See D. N. Kirk and M. P. Hartshorn, "Reaction Mechanisms," Elsevier Publishing Co., N.Y., 1968, page 294; E. P. Olweto et al., J. Am. Chem. Soc., 79, 3594 (1957); N. L. Wendler et al., ibid 78, 5027 (1956); and D. K. Fukushima et al., ibid 77, 6585 (1955).

Corticoids and 17α-hydroxyprogesterones both contain the Δ$^4$-3-ketone functionality in ring A. This α,β-unsaturated ketone undergoes enol acylation at C-3 during the usual acid catalyzed acylation at C-17. See U.S. Pat. Nos. 3,678,082; 2,753,360, Example 2; and U.S. Pat. No. 3,061,616, Example 8 as well as C. Djerassi et al., J. Am. Chem. Soc., 77, 3826 (1955) and R. Vitlotti et al., ibid, 81, 4566 (1959). The C-3 acylate must then be hydrolyzed to obtain the Δ$^4$-3-keto ring A structure. These extra steps are certainly undesirable in any event, but with the corticoids the 3-enolization produces additional problems. The acylated product (3,17,21-triacylate) upon hydrolysis condition sufficient to hydrolyze the C-3 acylate also hydrolyzes the C-21 acylate. When this occurs it is followed by migrations of the C-17 acylate to C-21 with further hydrolysis, etc.

The ring A functionality, Δ$^{1,4}$-3-keto undergoes irreversible dienone phenol rearrangement under acidic conditions (see Kirk, ibid, page 277) producing unwanted side product.

Another undesirable side reaction occurs with C-17 allylic and propargyl alcohols which eliminate under acidic acylation conditions.

U.S. Pat. No. 3,998,701 claims a process for preparing steroidal 17-esters of the corresponding 17α,21-dihydroxy 21-phosphate. This process by virtue of the requirement for a 21-phosphate is limited to corticoids and is not applicable to 17α-hydroxyprogesterones. An additional disadvantage to this process is that after C-17 acylation the C-21 phosphate group must be hydrolyzed enzymatically.

British Pat. No. 868,303, Example V, discloses the preparation of the caproate ester of 6α-methyl-17α-hydroxyprogesterone using caproic anhydride and p-TSA. This process took 60 hours and required heating on a steam bath.

A. J. Fatiadi, Carbohyd. Res., 6, 237 (1968) reported using acetic anhydride and anhydrous phosphoric acid to acylate various alcohols including, " . . . sterically hindered secondary alcohols, and tertiary alcohols; . . . ". Table I on page 238 disclosed the various alcohols which were acylated—none are tertiary alcohols. As stated in the first sentence of Fatiadia's article, he was looking to find an acylation agent for enolic compounds. The 17α-hydroxy group, in the steroids of the present invention, is not an enolic group.

U.S. Pat. No. 3,678,082 claims a process for acylating 17α-ethynyl-17β-hydroxy steroids by use of 4-(dimethylamino)pyridine. The catalyst in U.S. Pat. No. 3,678,082 is an organic base whereas the catalyst in the present invention is a phosphoric acid-type compound.

Offenlegungsschrift No. 2,055,221 discloses a process for acylating 17α-hydroxypregnanes in high yields by use of an anhydride or acid chloride with anhydrous stannic chloride (SnCl$_4$).

SUMMARY OF THE INVENTION

Disclosed in a process for the preparation of a compound of the formula:

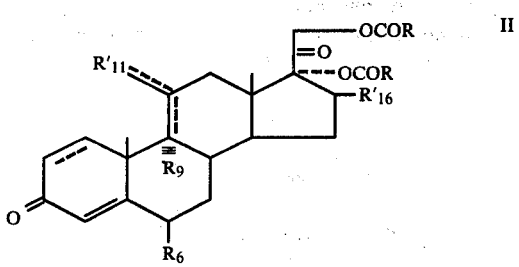

which comprises acylating a compound of the formula:

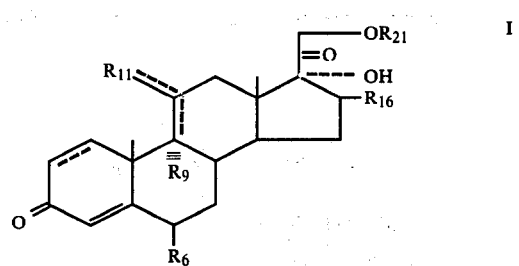

with an acylating agent selected from the group consisting of compounds of the formulas (RCO)$_2$O or RCOX and when the acylating agent is RCOX at least one equivalent of a base per equivalent of RCOX is required, and a phosphate catalyst.

Also disclosed is a process for the preparation of a compound of the formula:

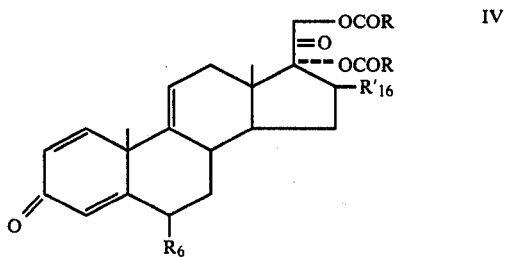

which comprises acylating a compound of the formula:

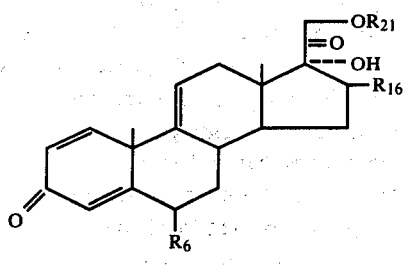

III

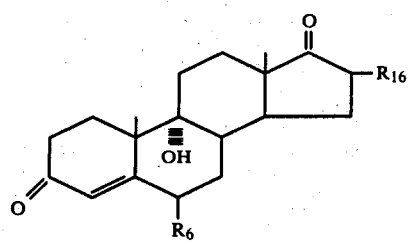

VII with an acylating agent selected from the group consisting of the compounds of the formula $(RCO)_2O$ or RCOX and when the acylating agent is RCOX at least one equivalent of base per equivalent of RCOX is required, and a phosphate catalyst with the proviso that when the phosphate catalyst is phosphoric acid, a buffering system which has 1–3 equivalents of base per equivalent of phosphoric acid is present.

Further disclosed is a process for the preparation of a compound of the formula:

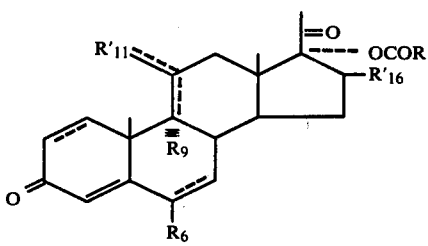

VI with an acylating agent selected from the group consisting of compounds of the formulas $(RCO)_2O$ or RCOX and when the acylating agent is RCOX at least one equivalent of base per equivalent of RCOX is required, and a phosphate catalyst.

Also disclosed is a process for the preparation of a compound of the formula:

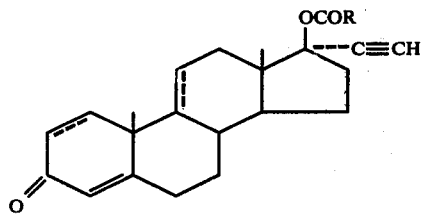

X which comprises acylating a compound of the formula:

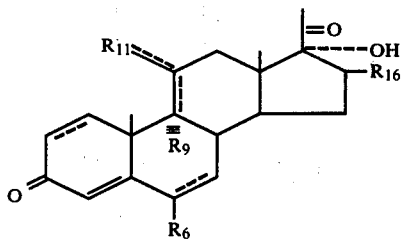

V

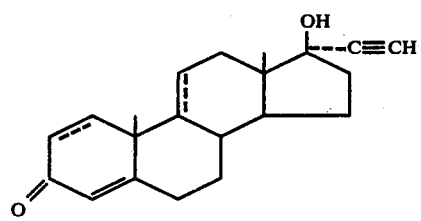

IX with an acylating agent selected from the group consisting of compounds of the formulas $(RCO)_2O$ or RCOX and when the acylating agent is RCOX at least one equivalent of base per equivalent of RCOX is required, and a phosphate catalyst.

Also disclosed is a process for the preparation of a compound of the formula:

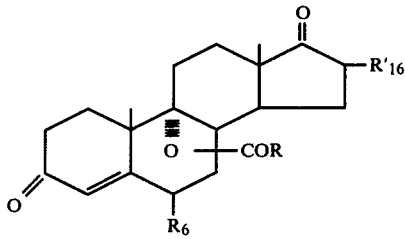

VIII with an acylating agent selected from the group consisting of the compounds of the formulas $(RCO)_2O$ or RCOX and when the acylating agent is RCOX at least one equivalent of base per equivalent of RCOX is required, and a phosphate catalyst with the proviso that when a phosphate catalyst is phosphoric acid a buffering system which has 1–3 equivalents of base per equivalent of phosphoric acid is present.

Disclosed is a process for the preparation of a compound of the formula:

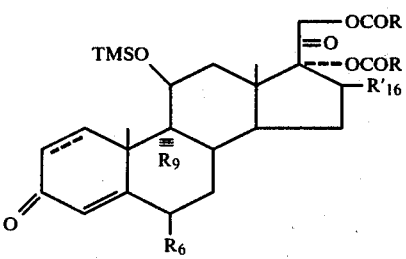

XII which comprises acylating a compound of the formula:

which comprises acylating a compound of the formula:

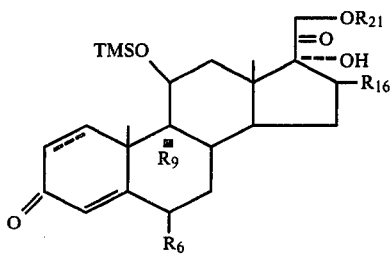

with an acylating agent selected from the group consisting of compounds of the formulas (RCO)₂O or RCOX and when the acylating agent is RCOX at least one equivalent of a base per equivalent of RCOX is required and a phosphate catalyst, with the proviso that when the phosphate catalyst is phosphoric acid, a buffering system which has 1–3 equivalents of base per equivalent of phosphoric acid is present.

The definitions and explanations below are for the terms as used throughout the entire patent application including both the specification and the claims.

R is a hydrogen atom, alkyl of 1 thru 6 carbon atoms, cycloalkyl of 5 thru 7 carbon atoms, phenyl substituted with 0 thru 3 substituents which are the same or different and are a chlorine atom or methyl, methoxy or nitro group.

$R_6$ is a hydrogen, α or β fluorine, or α or β chlorine atom or α or β methyl, methylene or β —CH₂—N(R′₆)₂ group.

$R'_6$ is alkyl of 1 thru 3 carbon atoms, phenyl or phenyl substituted in the para position with a chlorine atom, methyl, methoxy or nitro group with the proviso that both $R'_6$'s cannot be aromatic.

$R_9$ is a hydrogen, fluorine, chlorine, or bromine atom.

$R_{11}$ is (H), (H,H), (H, α —OH), (H, β —OH), or (O).

$R'_{11}$ is (H), (H,H), (H, α —OCOR), (H, β —OCOR) or (O).

$R_{16}$ is a hydrogen atom or α or β-methyl, methylene, or α-hydroxyl group.

$R'_{16}$ is a hydrogen atom or α or β-methyl, methylene, or α —OCOR group.

$R_{21}$ is a hydrogen atom or —COR group.

X is a chlorine or bromine atom.

--- is a single or double bond.

A phosphate catalyst is a phosphorus containing compound which produces acylation of a tertiary alcohol group in a Δ⁴-3-keto steroid with less than 15% 3-enol acylation when the Δ⁴-3-keto tertiary steroidal alcohol is reacted with an acylating agent selected from the group consisting of compounds of the formulas (RCO)₂O or RCOX and when the acylating agent is RCOX at least on equivalent of a base per equivalent of RCOX is required, and with the proviso that when the phosphate catalyst is phosphoric acid and the Δ⁴-3-keto tertiary steroidal alcohol is a Δ$^{1,4,9(11)}$-triene (III), a propargyl alcohol (IX) or an 11β-TMS derivative (XI), a buffering system which has 1–3 equivalents of base per equivalent of phosphoric acid is present.

All temperatures are in degrees Centigrade.

TLC refers to thin layer-chromatography.

THF refers to tetrahydrofuran.

DMF refers to dimethylformamide.

p-TSA refers to p-toluenesulfonic acid.

TMS refers to trimethylsilyl.

NMR refers to nuclear (proton) magnetic resonance spectroscopy.

UV refers to ultraviolet spectroscopy. $[\alpha]_D^{25}$ refers to the angle of rotation of plane polarized light (specific optical rotation) at 25° with the sodium D line (5893A).

When solvent pairs are used, the ratio of solvents used are volume/volume (v/v).

DETAILED DESCRIPTION OF THE INVENTION

The 17α-hydroxy steroidal reactants (I, III, V, XI), the 9α-hydroxy steroids (VII) as well as the propargyl alcohols (IX) are either well known to those skilled in the art or can readily be prepared from known compounds by methods well known to those skilled in the art.

Charts A, B, and C disclose the general process of the present invention.

CHART A

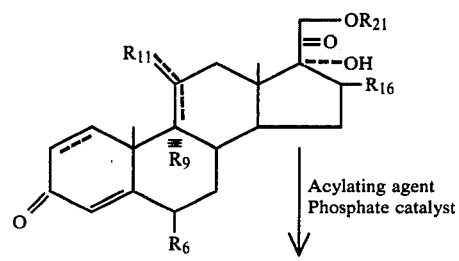

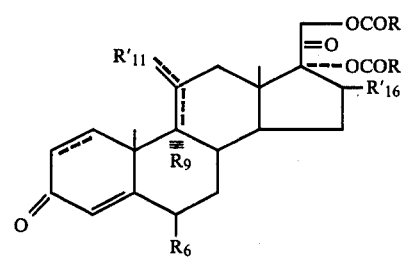

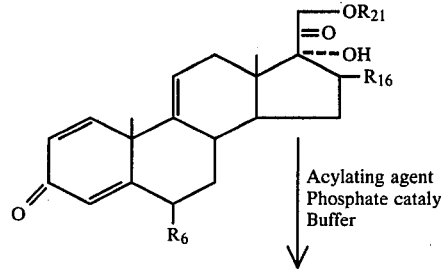

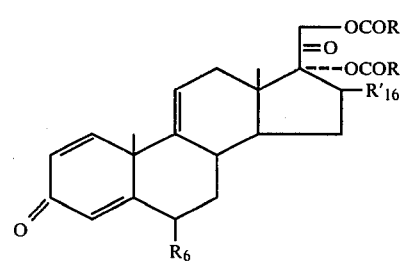

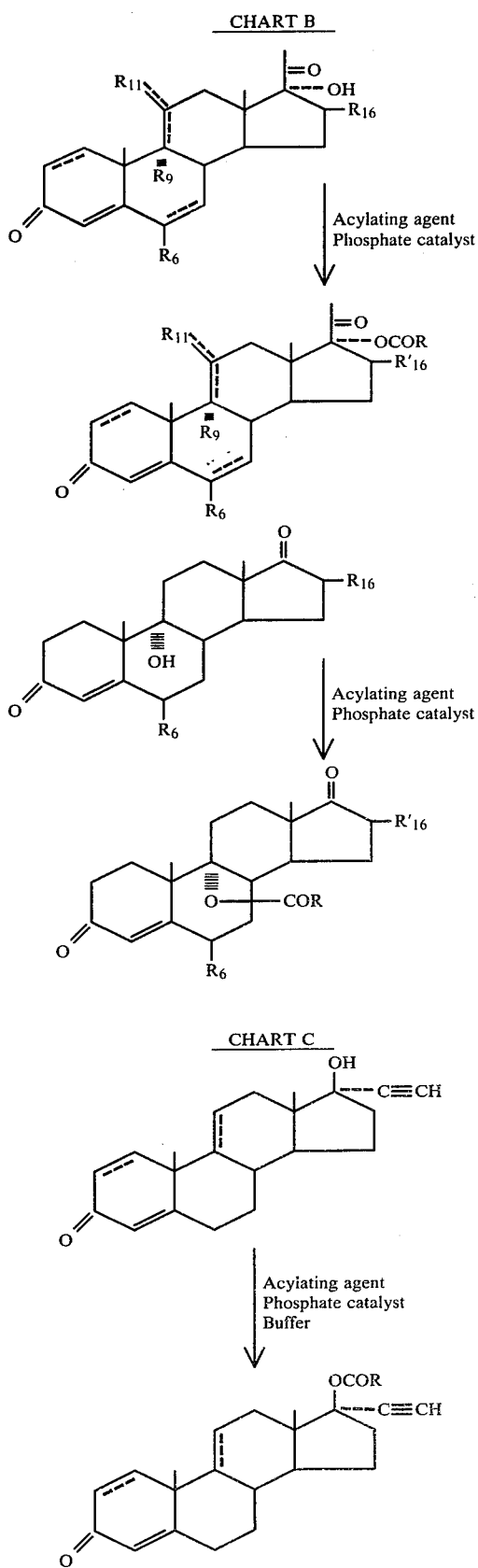

CHART B

CHART C

For the steroids (I, III, V, VII and IX) it is preferred that $R_6$ be hydrogen, fluorine, α-methyl (when possible), β—[—CH$_2$—N(R'$_6$)$_2$] or methylene. It is preferred that (R'$_6$)$_2$ is methyl-phenyl or ethyl-phenyl. It is preferred that $R_9$ (when present) be a hydrogen or fluorine atom. It is preferred that $R_{11}$ be (H), ($\Delta^{9(11)}$), (H,H) or (H, β —OH). It is preferred that $R_{16}$ be a hydrogen atom or β-methyl group. These $\Delta^4$-3-keto steroids may have an additional carbon-carbon double bond for example, $\Delta^1$, $\Delta^6$ or $\Delta^{9(11)}$ but the 17α-hydroxy steroid (I or V) cannot have a total of more than 2 carbon-carbon double bonds.

The tertiary steroidal alcohols (I, V, and VII) are acylated by reacting them with either an anhydride (RCO)$_2$O, or an acid halide, RCOX in the presence of a phosphate catalyst. When the acylating agent is RCOX a base must also be present. Suitable bases include, for example, the sodium or potassium salt of RCOO$^{\ominus}$, triethylamine, and pyridine. One equivalent of base/equivalent of RCOX is preferred. When the salt RCOO$^{\ominus}$ is used it is preferred that R correspond to the R of the acetylating agent. No base is necessary when the acylating agent is an anhydride.

It is preferred that the acetylating agent be an anhydride. It is preferred that the anhydride be selected from the group consisting of acetic, propionic, benzoic and caproic anhydrides. It is more preferred that the acetylating agent be acetic anhydride. However, also suitable are the anhydrides where the R's are connected together to form a cyclic anhydride selected from the group consisting of succinic, maleic, phthalic or glutaric anhydrides.

It is preferred that the phosphate catalyst be selected from the group consisting of phosphoric acid, mono- and dialkyl phosphate esters where the alkyl group is 1 thru 4 carbon atoms. It is more preferred that the phosphate catalyst be phosphoric acid.

The reaction medium requires that the phosphate catalyst be anhydrous. Therefore, anhydrous phosphoric acid can be used or aqueous phosphoric acid with sufficient acylating agent to react with the water present and produce an anhydrous medium. For economy sake, 85% phosphoric acid is preferred.

One skilled in the art could readily determine without any undue experimentation whether or not a given phosphorous containing compound is a phosphate catalyst within the meaning of that term with regards to the present invention. A steroid within the scope of the formulas (I, III, V, VII and IX) is reacted with an acetylating agent (and base if necessary) and the phosphorous containing compound under the reaction conditions to be described infra and the amount of 3-enol acylate is quantitatively determined by methods well known to those skilled in the art. If the amount of 3-enol acylate is less than 15%, the phosphorous containing compound is a phosphate catalyst.

While various amounts of the reactants are operable it is preferred that 1-8 equivalents of anhydride or acid halide and 1-4 equivalents of phosphoric acid per equivalent of steroid (I, V, or VII) be used. However, 1-50 equivalents of anhydride or acid halide and 0.01-50 equivalents of phosphoric acid are suitable. When the acid halide is the acylating agent, at least 1 equivalent of base per equivalent of acid halide is utilized. It is preferred that 1-2 equivalents of base be used.

Co-solvents may be utilized when solubility permits as is well known to those skilled in the art. The acid corresponding to the acid anhydride or acid halide may be used. For example, when the acetylating agent is acetic anhydride the co-solvent, if one is utilized, is preferably acetic acid. Other suitable co-solvents depending on solubility are, for example, THF, DMF, methylene chloride and ethyl acetate.

The reaction may be performed in the temperature range of −10° to 120°, preferably 25°–100°. The reaction time may vary from 1–36 hours. The reaction temperature, reaction time and quantity of phosphate catalyst are all interrelated and changing one affects the others. For instance, increased quantities of phosphate catalyst shorten reaction times.

The 1,4,9(11)-triene system of the steroid (III) is very acid sensitive. When the phosphate catalyst is phosphoric acid dienone-phenol rearrangement occurs unless the reaction medium is buffered. Therefore, when phosphoric acid is used the 1,4,9(11)-triene steroids (III) are bufferred and the tertiary alcohol undergoes acylation without 3-enol acylation or dienone phenol rearrangement.

Suitable buffers include bases such as the alkali metal salts of phosphoric acid such as potassium dibasic phosphate ($K_2HPO_4$), sodium tribasic phosphate ($Na_3PO_4$), triethylamine, pyridine, and the sodium and potassium salts of the acid corresponding to the acylating agent. For example, if the acylating agent is acetic anhydride a suitable base is potassium acetate. The buffer consists of 1–3 equivalents of base per equivalent of phosphoric acid, preferably 2–3 equivalents of base per equivalent of phosphoric acid. Yields of 84% are obtained by using mole ratios of 1,4,9(11)-triene steroidal tertiary alcohol (III)-phosphoric acid-acetylating agent-buffer of 1-4-12-8. See Example 7.

Chart C discloses the acylation of the 17β-hydroxy group of ethisterone-type compounds (IX). This tertiary alcohol group is also acid sensitive. Propargylic alcohols (e.g., the 17α-ethinyl-17β-hydroxy group) eliminate under acid conditions. For example, $\Delta^{9(11)}$-ethisterone is converted to the corresponding 17β-acetate in greater than 50% yield by the process of the present invention without buffering. With buffering, the yields are increased. The acylation process of the present invention for the propargylic alcohols (IX) is the same as for the 1,4,9(11)-triene steroidal tertiary alcohols (III).

Chart D discloses a process for the preparation of an 11β-hydroxy-17,21-diacylated steroid. An 11β,17α,21-trihydroxy steroid has the 11β-hydroxyl group protected by reacting the trihydroxy steroid with TMS chloride as is known to those skilled in the art to give the steroid (XI). The protected steroid (XI) is then acylated by the process of the present invention including the buffer to produce the 17,21-diacylated steroid (XII). The TMS group is then removed from the steroid (XII) by methods well known to those skilled in the art to give an 11β-hydroxy-17,21-diacylated steroid.

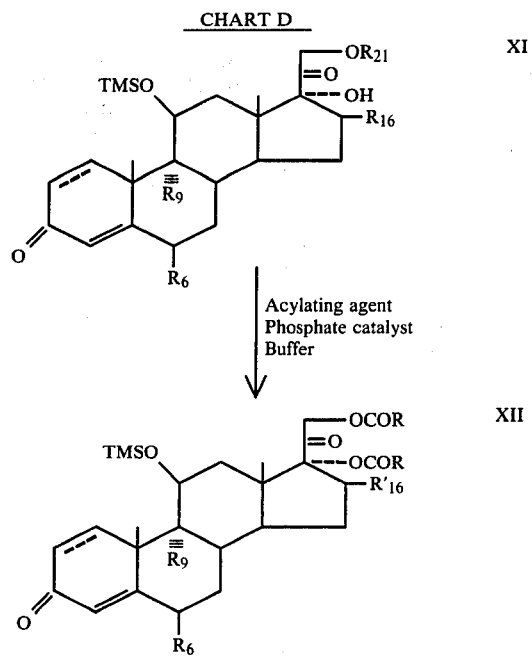

CHART D

The process of the present invention produces 17-acylated corticoids (II, IV and XII), 17α-hydroxyprogesterones (VI), 9-acylated 9α-hydroxyandrostenediones (VIII) and 17-acylated ethisterone-type compounds (X) in high yields using mild conditions with little if any of the undesired 3-enol acylate from the $\Delta^4$-3-keto steroids or dieneone-phenol rearrangement from the $\Delta^{1,4}$-steroids. In view of all the prior art processes the results of the present invention are indeed surprising and unexpected.

The acylated tertiary alcohols of the present invention are useful either as therapeutically active compounds or as intermediates in the synthesis of therapeutically active compounds.

The 17-acylated corticoids (II) are useful as topical anti-inflammatory agents as is well known to those skilled in the art. The 17-acylated corticoids (II) without a C-16 substituent ($R_{16}$ is a hydrogen atom) can be transformed to the corresponding $\Delta^{16}$-corticoid by the process of U.S. Pat. No. 3,631,076. The $\Delta^{16}$-corticoids are useful as anti-inflammatory and anti-allergenic agents as disclosed in U.S. Pat. No. 3,631,076. The $\Delta^{16}$ compounds can also be readily converted to 16-substituted compounds such as betamethasone [Taub et al., J. Am. Chem. Soc., 80, 4435 (1958); Oliveto et al., ibid 80, 6688 (1958); and Taub et al., ibid, 82, 4012 (1960)] and triamcinolone [S. Bernstein et al., J. Am. Chem. Soc., 78, 5693 (1956)]. For example, by the process of the present invention 17α,21-dihydroxypregna-4,9(11)-diene-3,20-dione 21-acetate (I) is converted to 17α,21-dihydroxypregna-4,9(11)-diene-3,20-dione 17,21-diacetate (II) in virtually quantitative yields. The diacetate (II) is then converted to 21-hydroxypregna-4,9(11),16-triene-3,20-dione 21-acetate by the general process of U.S. Pat. No. 3,631,076. This $\Delta^{16}$-steroid can then be transformed to various topical anti-inflammatory steroids by methods well known to those skilled in the art.

Further, the process of the present invention is useful when applied to a reactant such as 6α-fluoro-17α,21-dihydroxy-16β-methylpregna-4,9(11)-diene-3,20-dione 21-acetate [U.S. Pat. No. 3,980,778, Compound (2)] to transform it to 6α-fluoro-17α,21-dihydroxy-16β-methylpregna-4,9(11)-diene-3,20-dione 17,21-diacetate [U.S. Pat. No. 3,980,778, Compound (3)] in very high yields. See Example 6.

The 1,4,9(11)-triene corticoids (IV) can be reacted with a brominating agent to form the 9α-bromo-11β-hydroxy steroid which then can be reacted to form the 9,11-epoxide. The epoxide is opened by reaction with hydrogen fluoride (HF) to form the $\Delta^{1,4}$-9α-fluoro-11β-hydroxy corticoids (II) which are useful as topical anti-inflammatory agents. See U.S. Pat. No. 3,980,778, Examples 7 and 8.

The 17-acylated 17α-hydroxyprogesterones (VI) are useful as progestational agents. For example, see 17α-hydroxyprogesterone caproate, 17α-hydroxy-6α-methylprogesterone acetate, 17α-hydroxy-6-methyl-16-methylenepregna-4,6-diene-3,20-dione acetate.

The 9-acylated 9α-hydroxyandrostenediones (VIII) are converted by pyrolysis to $\Delta^{9(11)}$-androstenedione. $\Delta^{9(11)}$-androstenedione can be converted to $\Delta^{9(11)}$-ethisterone and then to various 17α-hydroxyprogesterones and corticoids by the processes of U.S. Pat. No. 4,041,055.

The 17-acylated propargylic alcohols (X) are useful as intermediates in the synthesis of corticoids and cardenolides, see Tetrahedron Letters 13, 987 (1976).

EXAMPLES

The invention may be more fully understood from the following examples which are illustrative of the process and compounds of the present invention but are not to be construed as limiting.

EXAMPLE 1

17α,21-Dihydroxypregna-4,9(11)-diene-3,20-dione 17,21-diacetate [Formula II: $R_6$, $R_9$ and $R'_{16}$ are hydrogen atoms; $R'_{11}$ is (H); R is methyl; --- in ring A is a single bond and --- in ring C is a double bond]

Refer to Chart A.

Phosphoric acid (85%, 15.3 g., d=1.68) is added to acetic acid (135 ml.). This mixture is added slowly to acetic anhydride (50 ml.) and the temperature is adjusted to 38°. 17α,21-Dihydroxypregna-4,9(11)-diene-3,20-dione 21-acetate (I, U.S. Pat. No. 4,041,055, Example 66, 50 g.) is added with stirring and the reaction heated to 75° over 15 minutes. The reaction is followed by TLC (chloroform:—acetone, 95:5). The reaction is complete after 110 minutes, TLC showing only traces of starting material and enol acetate product. The reaction is cooled over 1 hour to 26°. Sodium carbonate (50 ml., 20%) is slowly added with stirring, the resulting mixture is added to water (600 ml.), stirred 15 minutes and filtered. The resulting crystals are washed thoroughly with water (3×100 ml.) until the filtrate is neutral. The crystalline material is dried by passing dry nitrogen through it to yield the title compound, 54.08 g. (97.5% chemical yield), m.p. 224°–229.5°. $[\alpha]_D$+49.5° (chloroform).

EXAMPLE 2

11β,17α,21-Trihydroxypregna-1,4-diene-3,20-dione 11,17,21-triacetate [Formula II: $R_6$, $R_9$ and $R'_{16}$ are hydrogen atoms; $R'_{11}$ is (H, β —OCOR); R is methyl; --- in ring A is a double bond and --- in ring C is a single bond]

Refer to Chart A.

Phosphoric acid (85%, 0.065 ml.) is added to acetic acid (0.2 ml.) followed by acetic anhydride (0.18 ml.) 11β,17α,21-trihydroxypregna-1,4-diene-3,20-dione 21-acetate (I, The Merck Index, 9th Edition, Merck and Co., Rahway, NJ. U.S.A., 1976, #7510, 0.1 g.) is then added. After 7 hours at about 20°–25° water is added and the precipitate develops. The precipitate is filtered, washed with water and dried to give the title compound, m.p. 119°–126°.

EXAMPLE 3

11β,17α,21-Trihydroxypregn-4-ene-3,20-dione 11,17,21-triacetate [Formula II: $R_6$, $R_9$ and $R'_{16}$ are hydrogen atoms; $R'_{11}$ is (H, β —OCOR); R is methyl; --- in ring A is a double bond; --- in ring C is a single bond]

Refer to Chart A.

Following the general procedure of Example 2 and making non-critical variations but substituting 11β,17α,21-trihydroxypregn-4-ene-3,20-dione 21-acetate (I, Merck Index, #4675 and Steroids, Fieser and Fieser, Reinhold Publishing Co., London, 1959, page 607) the title compound is obtained.

EXAMPLE 4

17α,21-Dihydroxypregn-4-ene-3,20-dione 17,21-diacetate [Formula II: $R_6$, $R_9$ and $R'_{16}$ are hydrogen atoms; $R'_{11}$ is (H,H), R is methyl and --- in rings A and C are single bonds]

Refer to Chart A.

Following the general procedure of Example 1 and making non-critical variations but using 17α,21-dihydroxypregn-4-ene-3,20-dione 21-acetate (I, Steroids, Fieser and Fieser, page 656, 657) as the reactant, the title compound is obtained.

EXAMPLE 5

17α,21-Dihydroxypregna-1,4-diene-3,20-dione 17,21-diacetate [Formula II: $R_6$, $R_9$ and $R'_{16}$ are hydrogen atoms; $R'_{11}$ is (H,H), R is methyl; --- in ring A is a double bond and --- in ring C is a single bond]

Refer to Chart A.

Following the general procedure of Example 1 and making non-critical variations but using 17α,21-dihydroxypregna-1,4-diene-3,20-dione 21-acetate [I, J. Am. Chem. Soc., 72, 4081 (1950)] as the reactant, the title compound is obtained.

EXAMPLE 6

6α-Fluoro-17α,21-dihydroxy-16β-methylpregna-4,9(11)-diene-3,20-dione 17,21-diacetate [Formula II: $R_6$ is a fluorine atom; $R_{11}$ is (H); $R'_{16}$ is β methyl; R is methyl; --- in ring A is a single bond and --- in ring C is a double bond]

Refer to Chart A.

Following the general procedure of Example 1 and making non-critical variations but using 6α-fluoro-17α,21-dihydroxy-16β-methylpregna-4,9(11)-diene-3,20-dione 21-acetate (I, U.S. Pat. No. 3,980,778, Example 1) as the reactant the title compound is obtained.

EXAMPLE 7

17α,21-Dihydroxypregna-1,4,9(11)-triene-3,20-dione 17,21-diacetate [Formula IV: $R_6$ and $R'_{16}$ are hydrogen atoms; and R is methyl]

Refer to Chart A.

Phosphoric acid (85%, 5.6 ml.), acetic anhydride (30.4 ml.) and potassium acetate (15.7 g.) are added to acetic acid (10 ml.). The mixture is cooled to about 22° and 17α,21-dihydroxypregna-1,4,9(11)-triene-3,20- dione 21-acetate (III, U.S. Pat. No. 2,957,893, 7.7 g.) is added and the mixture heated to 70° for 3 days. Acetic acid (20 ml.) is added and the reaction mixture heated (70°–80°) for an additional 5.5 days. Neutral phosphate buffer (5%, 20 ml.) and water (300 ml.) are added forming a precipitate which is filtered, washed with water (125 ml.) and dried to yield the title compound, 7.19 g. (84.2% chemical yield), m.p. 186°–216°; $[\alpha]_D +3°$ (chloroform); UV (methanol) $\lambda max = 238$ m$\mu$ ($\epsilon = 16,650$).

EXAMPLE 8

17$\alpha$-Hydroxypregn-4-ene-3,20-dione 17-acetate [Formula VI: $R_6$, $R_9$ and $R'_{16}$ are hydrogen atoms; $R'_{11}$ is (H,H); R is methyl; --- in rings A, B, and C are single bonds]

Refer to Chart B.

Phosphoric acid (85%, 2.0 ml.) and acetic anhydride (8.53 ml.) are added to acetic acid (15 ml.). The temperature is adjusted to 18° and 17$\alpha$-hydroxyprogesterone (V, U.S. Pat. No. 3,000,883, 10 g.) and acetic acid (5 ml.) are added. After 26.5 hours at 29° water (50 ml.) is added and the mixture poured into water (250 ml.). The crystalline material is filtered, washed with water and dried to yield the title compound, 10.85 g. (96% chemical yield), m.p. 238°–240°; NMR (CDCl$_3$) 0.69, 1.20, 2.04, 2.10 and 5.73 $\delta$.

EXAMPLE 9

17$\alpha$-Hydroxy-6$\alpha$-methylpregn-4-ene-3,20-dione 17-acetate [Formula VI: $R_6$ is $\alpha$-methyl; $R_9$ and $R'_{16}$ are hydrogen atoms; $R'_{11}$ is (H,H); R is methyl and --- in rings A, B, and C is a single bond]

Refer to Chart B.

Following the general procedure of Example 8 and making non-critical variations but using 17$\alpha$-hydroxy-6$\alpha$-methylprogesterone [V, J. Am. Chem. Soc., 80, 2904 (1958)] as the reactant the title compound is obtained.

EXAMPLE 10

17$\alpha$-Hydroxy-6-methylenepregn-4-ene-3,20-dione 17-acetate [Formula VI: $R_6$ is methylene; $R_9$ and $R'_{16}$ are hydrogen atoms; $R'_{11}$ is (H,H); R is methyl and --- in rings A, B, and C are single bonds]

Refer to Chart B.

Phosphoric acid (85%, 5 ml.) and acetic anhydride (22 ml.) are added to acetic acid and cooled to 0°. 17$\alpha$-hydroxy-6-methyleneprogesterone (V, U.S. Pat. No. 3,642,840, Example 2, 5 g.) is added and the reaction mixture is maintained at 0° for 23 hours. Water (150 ml.) is added dropwise resulting in precipitation of crystalline material which is filtered, washed with water and dried to yield the title compound, 5.68 g. (101% chemical yield), m.p. 228.5°–230°; $[\alpha]_D +221°$ (chloroform); NMR (CDCl$_3$) 0.67, 1.09, 2.02, 2.04, 4.95, 5.05 and 5.88 $\delta$.

EXAMPLE 11

17$\alpha$-Hydroxy-6-methylpregna-4,6-diene-3,20-dione 17-acetate [Formula VI: $R_6$ and R are methyl; $R_9$ and $R'_{16}$ are hydrogen atoms; $R'_{11}$ is (H,H); --- in rings A and C is a single bond and --- in ring B is a double bond]

Refer to Chart B.

Following the general procedure of Example 10 and making non-critical variations but using 17$\alpha$-hydroxy-6-methylpregna-4,6-diene-3,20-dione (V, U.S. Pat. No. 2,891,079, Example 2) as the reactant, the title compound is obtained.

EXAMPLE 12

17$\alpha$-Hydroxy-6-methyl-16-methylenepregna-4,6-diene-3,20-dione 17-acetate [Formula VI: $R_6$ and R are methyl; $R_9$ is a hydrogen atom; $R'_{11}$ is (H,H); $R'_{16}$ is methylene; --- in ring B is a double bond and --- in rings A and C are single bonds]

Refer to Chart B.

Following the general procedure of Example 10 and making non-critical variations but substituting 17$\alpha$-hydroxy-6-methyl-16-methylenepregna-4,6-diene-3,20-dione (V, Merck Index #5637) as the reactant the title compound is obtained.

EXAMPLE 13

17$\alpha$-Hydroxy-6$\beta$-(N-methyl-N-phenylaminomethyl)-pregn-4-ene-3,20-dione 17-acetate [Formula VI: $R_6$ is $\beta$-(N-methyl-N-phenylaminomethyl); $R_9$ and $R'_{16}$ are hydrogen atoms; $R'_{11}$ is (H,H); --- in rings A, B, and C is a single bond and R is methyl]

Refer to Chart B.

17$\alpha$-Hydroxy-6$\beta$-(N-methyl-N-phenylaminomethyl)-pregn-4-ene-3,20-dione (V) is prepared by the process of U.S. Pat. No. 3,642,840, in particular by Examples 6 and 25.

The amino steroid (V, 5 g.) is added to a solution of phosphroic acid (85%, 2.3 ml.) and acetic anhydride (24 ml.) at 0°. The mixture is stirred at 0° for 24–30 hours. The mixture is worked up by the procedure of Example 8 to give the title compound.

EXAMPLE 14

17$\alpha$-Hydroxy-6$\beta$-(N-ethyl-N-phenylaminomethyl)-pregn-4-ene-3,20-dione 17-acetate [Formula VI: $R_6$ is $\beta$-(N-ethyl-N-phenylaminoethyl); $R_9$ and $R'_{16}$ are hydrogen atoms; $R'_{11}$ is (H,H); --- in rings A, B, and C is a single bond and R is methyl]

Refer to Chart B.

17$\alpha$-Hydroxy-6$\beta$-(N-ethyl-N-phenylaminomethyl)-pregn-4-ene-3,20-dione (V) is prepared by the process of U.S. Pat. No. 3,642,840 in particular Examples 6 and 25.

Following the general procedure of Example 13 and making non-critical variations but using 17$\alpha$-hydroxy-6$\beta$-(N-ethyl-N-phenylaminomethyl)-pregn-4-ene-3,20-dione as the reactant, the title compound is obtained.

EXAMPLE 15

9$\alpha$-Hydroxyandrost-4-ene-3,17-dione 9-acetate [Formula VIII: $R_6$ and $R'_{16}$ are hydrogen atoms; R is methyl and --- in ring A is a single bond]

Refer to Chart B.

Following the general procedure of Example 1 and making non-critical variations but substituting 9-hydroxyandrostenedione (VII, U.S. Pat. No. 4,035,236, Example 2) as the reactant the title compound is obtained.

EXAMPLE 16

17$\alpha$-ethinyl-17$\beta$-hydroxyandrost-4-ene-3-one 17-acetate [Formula X: --- in rings A and C are single bonds and R is methyl]

Refer to Chart C.

Following the general procedure of Example 7 and making non-critical variations but substituting 17$\alpha$-ethinyl-17$\beta$-hydroxyandrost-4-ene-3-one (U.S. Pat. No. 4,041,055, preparation 1) there is obtained the title compound.

We claim:
1. A process for the preparation of a compound of the formula:

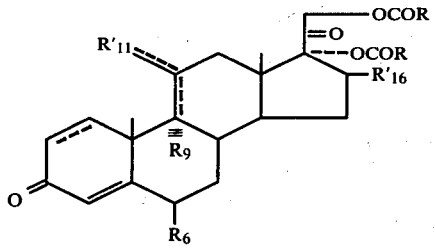

where $R_6$ is a hydrogen, $\alpha$ or $\beta$ fluorine or $\alpha$ or $\beta$ chlorine atom, or $\alpha$ or $\beta$ methyl, methylene or $\beta$ —CH$_2$—N(R'$_6$)$_2$ group; where R'$_6$ is alkyl of 1 thru 3 carbon atoms, phenyl or phenyl substituted in the para position with a chlorine atom, methyl, methoxy or nitro group with the proviso that both R'$_6$'s cannot be aromatic; where $R_9$ is a hydrogen atom; where R'$_{11}$ is (H), (H,H), (H, $\alpha$ —OCOR), (H, $\beta$ —OCOR) or (O); where R'$_{16}$ is a hydrogen atom or $\alpha$ or $\beta$ methyl, methylene, or $\alpha$ —OCOR group; where R is a hydrogen atom, alkyl of 1 thru 6 carbon atoms, cycloalkyl of 5 thru 7 carbon atoms, phenyl substituted with 0 thru 3 substituents which are the same or different and are a chlorine atom or methyl, methoxy or nitro group; where ⹀ is a single or double bond with the proviso that within rings A and C only one of ⹀ can be a double bond, which comprises acylating a compound of the formula:

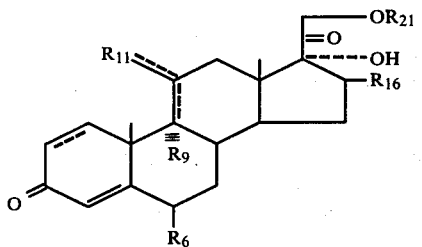

where $R_6$, $R_9$, and ⹀ are defined above having the same proviso as defined above; where $R_{11}$ is (H), (H,H), (H, $\alpha$ —OH), (H, $\beta$ —OH) or (O); where $R_{16}$ is a hydrogen atom or $\alpha$ or $\beta$ methyl, methylene or $\alpha$-hydroxyl group; where $R_{21}$ is a hydrogen atom or —OCOR group, where R is defined above; with an acylating agent selected from the group consisting of compounds of the formulas (RCO)$_2$O where the two R's can be connected to form a cyclic anhydride selected from the group consisting of succinic, maleic, phthalic or glutaric anhydride; or RCOX and when the acylating agent is RCOX at least 1 equivalent of a base per equivalent of RCOX is required, where X is a chlorine or bromine atom and where R is defined above, and a phosphate catalyst.

2. A process according to claim 1 where the phosphate catalyst is selected from the group consisting of phosphoric acid, mono- and dialkyl phosphate esters where the alkyl group is 1 thru 4 carbon atoms.

3. A process according to claim 2 where the phosphate catalyst is phosphoric acid.

4. A process according to claim 3 where the phosphoric acid is 80–90% phosphoric acid.

5. A process according to claim 1 where the acetylating agent is selected from the group consisting of acetyl chloride, propionyl chloride, benzoyl chloride and caproyl chloride; the base is the sodium or potassium salt of RCOO$^\ominus$, triethylamine, and pyridine and 1–2 equivalents of base are used where R is defined in claim 1.

6. A process according to claim 1 where the acetylating agent is (RCO)$_2$O.

7. A process according to claim 6 where the acetylating agent is selected from the group consisting of acetic anhydride, propionic anhydride, benzoic anhydride, and caproic anhydride.

8. A process according to claim 7 where the acetylating agent is acetic anhydride.

9. A process according to claim 1 where the compound of formula (II) is 17α,21-dihydroxypregna-4,9(11)-diene-3,20-dione 17,21-diacetate.

10. A process according to claim 1 where the compound of formula (II) is 11β,17α,21-trihydroxypregna-1,4-diene-3,20-dione 11,17,21-triacetate.

11. A process according to claim 1 where the compound of formula (II) is 11β,17α,21-trihydroxypregn-4-ene-3,20-dione 11,17,21-triacetate.

12. A process according to claim 1 where the compound of formula (II) is 17α,21-dihydroxypregn-4-ene-3,20-dione 17,21-diacetate.

13. A process according to claim 1 where the compound of formula (II) is 17α,21-dihydroxypregna-1,4-diene-3,20-dione 17,21-diacetate.

14. A process according to claim 1 where the compound of formula (II) is 6α-fluoro-17α,21-dihydroxy-16β-methylpregna-4,9(11)-diene-3,20-dione 17,21-diacetate.

15. A process for the preparation of 17α,21-dihydroxypregna-4,9(11)-diene-3,20-dione 17,21-diacetate which comprises acetylating 17α,21-dihydroxypregna-4,9(11)-diene-3,20-dione 21-acetate with acetic anhydride in the presence of phosphoric acid.

16. A process for the preparation of a compound of the formula:

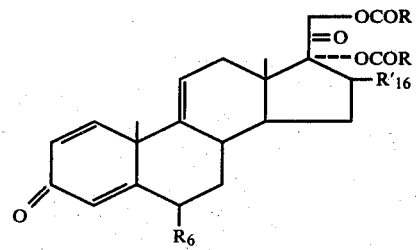

which comprises acylating a compound of the formula:

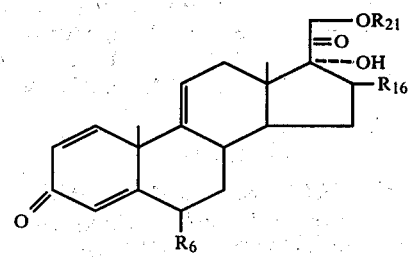

with an acylating agent selected from the group consisting of compounds of the formulas (RCO)$_2$O or RCOX and when the acylating agent is RCOX at least one equivalent of a base per equivalent of RCOX is required and a phosphate catalyst with the proviso that when the phosphate catalyst is phosphoric acid, a buffering system which has 1-3 equivalents of base per equivalent of phosphoric acid is present where $R_6$, $R'_{16}$, $R$, $R_{16}$, $R_{21}$ and X are defined in claim 1.

17. A process according to claim 16 where the phosphate catalyst is selected from the group consisting of phosphoric acid, mono- and dialkyl phosphate esters where the alkyl group is 1 thru 4 carbon atoms.

18. A process according to claim 17 where the phosphate catalyst is phosphoric acid and where the base of the buffer is selected from the group consisting of triethylamine, pyridine or the sodium and potassium salts of $RCOO^\ominus$ or phosphoric acid where R is defined in claim 1.

19. A process according to claim 18 where the phosphoric acid is 80-90% phosphoric acid and 2-3 equivalents of the base are utilized.

20. A process according to claim 16 where the acetylating agent is selected from the group consisting of acetyl chloride, propionyl chloride, benzoyl chloride, and caproyl chloride; the base is the sodium or potassium salt of $RCOO^\ominus$, triethylamine, and pyridine and 1 to 2 equivalents of base are used per equivalent of RCOX, where R is defined in claim 1.

21. A process according to claim 16 where the acetylating agent is $(RCO)_2O$.

22. A process according to claim 21 where the acetylating agent is selected from the group consisting of acetic anhydride, propionic anhydride, benzoic anhydride and caproic anhydride.

23. A process according to claim 22 where the acetylating agent is acetic anhydride.

24. A process according to claim 16 where the compound of formula (IV) is 17α,21-dihydroxypregna-1,4,9(11)-triene-3,20-dione 17,21-diacetate.

25. A process for preparing a compound of the formula:

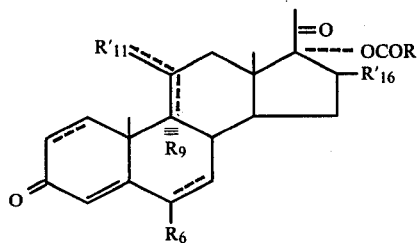

which comprises acylating a compound of the formula:

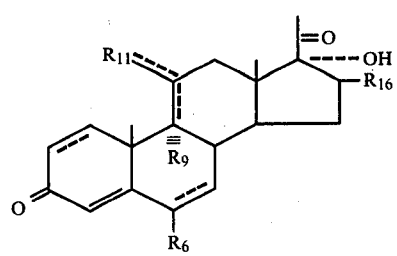

with an acylating agent selected from the group consisting of compounds of the formulas $(RCO)_2O$ or RCOX and when the acylating agent is RCOX at least one equivalent of base per equivalent of RCOX is required, and a phosphate catalyst where $R_9$ is a hydrogen, fluorine, chlorine or bromine atom and where $R_6$, $R_{11}$, $R'_{11}$, $R_{16}$, $R'_{16}$, $R$, --- and X are defined in claim 1 with the proviso that within rings A, B and C only one of --- can be a double bond.

26. A process according to claim 25 where the phosphate catalyst is selected from the group consisting of phosphoric acid, mono- and dialkyl phosphate esters where the alkyl group is 1 thru 4 carbon atoms.

27. A process according to claim 26 where the phosphate catalyst is phosphoric acid.

28. A process according to claim 27 where the phosphoric acid is 80-90% phosphoric acid.

29. A process according to claim 25 where the acetylating agent is selected from the group consisting of acetyl chloride, propionyl chloride, benzoyl chloride, and caproyl chloride; the base is the sodium, or potassium salt of $RCOO^\ominus$, triethylamine, and pyridine and 1 to 2 equivalents of base per equivalent of RCOX are used, where R is defined in claim 1.

30. A process according to claim 25 where the acetylating agent is $(RCO)_2O$.

31. A process according to claim 30 where the acetylating agent is selected from the group consisting of acetic anhydride, propionic anhydride, benzoic anhydride, and caproic anhydride.

32. A process according to claim 31 where the acetylating agent is acetic anhydride.

33. A process according to claim 25 where the compound of formula (VI) is 17α-hydroxypregn-4-ene-3,20-dione 17-acetate.

34. A process according to claim 25 where the compound of formula (VI) is 17α-hydroxy-6α-methylpregn-4-ene-3,20-dione 17-acetate.

35. A process according to claim 25 where the compound of formula (VI) is 17α-hydroxy-6-methylenepregn-4-ene-3,20-dione 17-acetate.

36. A process according to claim 25 where the compound of formula (VI) is 17α-hydroxy-6-methylpregna-4,6-diene-3,20-dione 17-acetate.

37. A process according to claim 25 where the compound of formula (VI) is 17α-hydroxy-6-methyl-16-methylenepregna-4,6-diene-3,20-dione 17-acetate.

38. A process according to claim 25 where the compound of formula (VI) is 17α-hydroxy-6β-(N-methyl-N-phenylaminomethyl)-pregn-4-ene-3,20-dione 17-acetate.

39. A process according to claim 25 where the compound of formula (VI) is 17α-hydroxy-6β-(N-ethyl-N-phenylaminomethyl)pregn-4-ene-3,20-dione 17-acetate.

40. A process for preparing a compound of the formula:

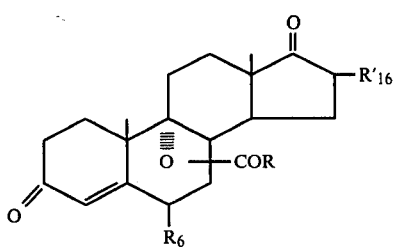

which comprises acylating a compound of the formula:

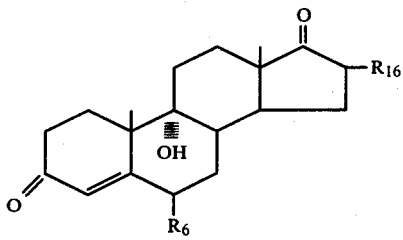

with an acylating agent selected from the group consisting of compounds of the formulas (RCO)₂O or RCOX and when the acylating agent is RCOX at least one equivalent of base per equivalent of RCOX is required, and a phosphate catalyst where R₆, R'₁₆, R, R₁₆, and X are defined in claim 1.

41. A process according to claim 40 where the phosphate catalyst is selected from the group consisting of phosphoric acid, mono- and dialkyl phosphate esters where the alkyl group is 1 thru 4 carbon atoms.

42. A process according to claim 41 where the phosphate catalyst is phosphoric acid.

43. A process according to claim 42 where the phosphoric acid is 80–90% phosphoric acid.

44. A process according to claim 40 where the acylating agent is selected from the group consisting of acetic anhydride, propionic anhydride, benzoic anhydride, and caproic anhydride.

45. A process according to claim 44 where the acylating agent is acetic anhydride.

46. A process according to claim 40 where the compound of formula (VIII) is 9α-hydroxyandrost-4-ene-3,17-dione 9-acetate.

47. A process for the preparation of a compound of the formula:

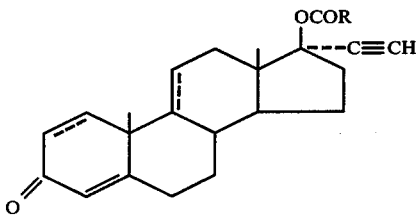

which comprises acylating a compound of the formula:

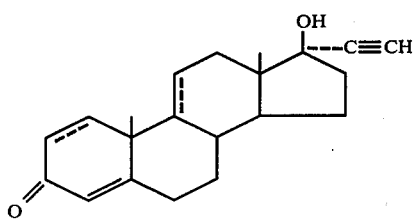

with an acylating agent selected from the group consisting of compounds of the formulas (RCO)₂O or RCOX and when the acylating agent is RCOX at least one equivalent of a base per equivalent of RCOX is required, and a phosphate catalyst with a proviso that when the phosphate catalyst is phosphoric acid a buffering system which has 1–3 equivalents of base per equivalent of phosphoric acid is present, where⎯⎯⎯is defined in claim 1.

48. A process according to claim 47 where the phosphate catalyst is selected from the group consisting of phosphoric acid, mono- and dialkyl phosphate esters where the alkyl group is 1–4 carbon atoms.

49. A process according to claim 48 where the phosphate catalyst is phosphoric acid and when the base of the buffer is selected from the group consisting of triethylamine, pyridine or the sodium and potassium salts of RCOO⊖ or phosphoric acid where R is defined in claim 1.

50. A process according to claim 49 where the phosphoric acid is 80–90% phosphoric acid and 2 to 3 equivalents of the base are used.

51. A process according to claim 47 where the acylating agent is selected from the group consisting of acetyl chloride, propionyl chloride, benzoyl chloride, and caproyl chloride; the base is the sodium or potassium salt of RCOO⊖, triethylamine, and pyridine and 1 to 2 equivalents of base are used per equivalent of RCOX where R is defined in claim 1.

52. A process according to claim 47 where the acetylating agent is (RCO)₂O.

53. A process according to claim 52 where the acylating agent is selected from the group consisting of acetic anhydride, propionic anhydride, benzoic anhydride, and caproic anhydride.

54. A process according to claim 53 where the acylating agent is acetic anhydride.

55. A process according to claim 47 where the compound of formula (X) is 17α-ethinyl-17β-hydroxyandrost-4-ene-3-one 17-acetate.

56. A process for the preparation of a compound of the formula:

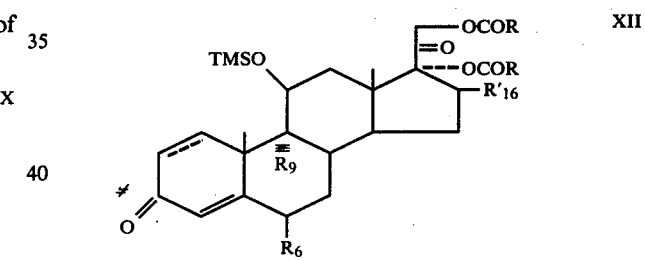

which comprises acylating a compound of the formula:

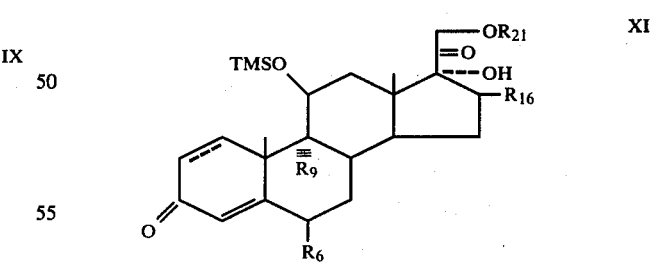

with an acylating agent selected from the group consisting of compounds of the formulas (RCO)₂O or RCOX and when the acylating agent is RCOX at least one equivalent of a base per equivalent of RCOX is required and a phosphate catalyst, with the proviso that when the phosphate catalyst is phosphoric acid, a buffering system which has 1–3 equivalents of base per equivalent of phosphoric acid is present where R, R₆, R₁₆, R'₁₆, R₂₁ and⎯⎯⎯are defined in claim 1; where R₉ is as defined in claim 25 and where TMS is trimethylsilyl.

57. A process according to claim 56 where the phosphate catalyst is selected from the group consisting of phosphoric acid, mono- and dialkyl phosphate esters where the alkyl group is 1 thru 4 carbon atoms.

58. A process according to claim 57 where the phosphate catalyst is phosphoric acid.

59. A process according to claim 58 where the phosphoric acid is 80–90% phosphoric acid.

60. A process according to claim 57 where the acetylating agent is selected from the group consisting of acetyl chloride, propionyl chloride, benzoyl chloride and caproyl chloride; the base is the sodium or potassium salt of $RCOO^{\ominus}$, triethylamine and pyridine and 1–2 equivalent of base are used where R is defined in claim 1.

61. A process according to claim 57 where the acetylating agent is $(RCO)_2O$.

62. A process according to claim 61 where the acetylating agent is selected from the group consisting of acetic anhydride, propionic anhydride, benzoic anhydride, and caproic anhydride.

63. A process according to claim 62 where the acetylating agent is acetic anhydride.

64. A process according to claim 1 where $=$ in ring A is a single bond.

65. A process according to claim 64 where the phosphate catalyst is selected from the group consisting of phosphoric acid, mono- and dialkyl phosphate esters where the alkyl group is 1 thru 4 carbon atoms.

66. A process according to claim 65 where the phosphate catalyst is phosphoric acid.

67. A process according to claim 66 where the phosphoric acid is 80–90% phosphoric acid.

68. A process according to claim 64 where the acetylating agent is selected from the group consisting of acetyl chloride, propionyl chloride, benzoyl chloride and caproyl chloride; the base is the sodium or potassium salt of $RCOO^{\ominus}$, triethylamine, and pyridine and 1–2 equivalents of base are used where R is defined in claim 1.

69. A process according to claim 64 where the acetylating agent is $(RCO)_2O$.

70. A process according to claim 69 where the acetylating agent is selected from the group consisting of acetic anhydride, propionic anhydride, benzoic anhydride, and caproic anhydride.

71. A process according to claim 70 where the acetylating agent is acetic anhydride.

72. A process according to claim 64 where the compound of formula (II) is 17α,21-dihydroxy-16β-methyl-pregna-4,9(11)-diene-3,20-dione 17,21-diacetate.

73. A process according to claim 25 where $=$ in ring A is a single bond.

74. A process according to claim 47 where $=$ in ring A is a single bond.

75. A process according to claim 56 where $=$ in ring A is a single bond.

* * * * *